United States Patent
Jones et al.

(10) Patent No.: US 8,586,371 B2
(45) Date of Patent: Nov. 19, 2013

(54) OPTICAL SENSORS INCLUDING SURFACE MODIFIED PHASE-CHANGE MATERIALS FOR DETECTION OF CHEMICAL, BIOLOGICAL AND EXPLOSIVE COMPOUNDS

(75) Inventors: James Everett Pendell Jones, Baltimore, MD (US); Anthony Bresenhan Kaye, Herndon, VA (US); Richard Forsberg Haglund, Brentwood, TN (US); David Edward Cliffel, Nashville, TN (US); David Wright, Nashville, TN (US)

(73) Assignees: Exelis Inc., McLean, VA (US); Vanderbilt University, Nashville, TN (US)

( * ) Notice: Subject to any disclaimer, the term of this patent is extended or adjusted under 35 U.S.C. 154(b) by 470 days.

(21) Appl. No.: 12/712,048

(22) Filed: Feb. 24, 2010

(65) Prior Publication Data
US 2011/0205542 A1    Aug. 25, 2011

(51) Int. Cl.
  *G01N 33/00*        (2006.01)
(52) U.S. Cl.
  USPC .............. 436/104; 436/106; 422/50; 422/402
(58) Field of Classification Search
  None
  See application file for complete search history.

(56) References Cited

U.S. PATENT DOCUMENTS 6,906,842 B2    6/2005    Agrawal et al.

FOREIGN PATENT DOCUMENTS

| EP | 1 295 169 B1 | 6/2008 |
| WO | 2008087077 A1 | 7/2008 |
| WO | 2010141168 A1 | 12/2010 |

OTHER PUBLICATIONS

Ziegler, Jed I. et al., Interface effects in hybrid gold/vanadium dioxide nanostructures, 2009, Proceding of SPIE, vol. 7394, pp. 73940Q-1 to 73940Q-10.*
Dahan, A. et al. Dendrons and Dendritic catalysts immobilized on solid support: synthesis and dendritic effects in catalysis, 2005, JOurnal of Polymer Science: Part A: Polymer Chemistry, vol. 43, pp. 235-262.*
Wang, D. et al. Metal ion catalytic sites in a series of polyamindamine dendrimers: activity towards phophate esters, and hydrogen peroxide, 2001, Symposia papers presented before the division of environmental chemistry, American chemical Society, San Diego, CA Apr. 1-5, 2001. pp. 282-285.*
Burkhardt, W. et al. W- and F-doped VO2 films studied by photoelectron spectrometry, 1999, Thin Solid Films, vol. 345, pp. 229-235.*

(Continued)

*Primary Examiner* — Robert Xu
(74) *Attorney, Agent, or Firm* — Edell, Shapiro & Finnan, LLC (57) ABSTRACT

A sensor device includes an optical limiting structure including a metal layer with at least one metal particle having a size no greater than about 1500 nanometers, and a phase-change material layer disposed adjacent at least a portion of the metal layer, the phase-change material layer including a phase-change material, and a dendritic-metal layer disposed over at least a portion of the phase-change material layer of the optical limiting structure, the dendritic-metal layer including an organic compound including branching chain amino acid groups attached to a metal structure. The optical limiting structure is configured to transition from a first optical state to a second optical state when the phase-change material is heated above a critical temperature, with transmittance of light at a predetermined wavelength through the optical limiting structure being lower at the second optical state of the optical limiting structure in relation to the first optical state of the optical limiting structure.

20 Claims, 4 Drawing Sheets

(56) References Cited

OTHER PUBLICATIONS

Xu et al., "Surface Plasmon Resonance of Silver Nanoparticles on Vanadium Dioxide", J. Phys. Chem. B, vol. 110, No. 5, 2006, pp. 2051-2056.

Xu et al., "Tunable Optical Properties of nano-AU on Vanadium Dioxide", Optics Communications 282, 2009, pp. 896-902.

EP Search Report dated Jun. 24, 2011 received in corresponding EP11155023.2.

Weiping Wang, et al., "Dynamic Optical Limiting Experiments on Vanadium Dioxide and Vanadium Pentoxide Thin Films Irradiated by a Laser Beam", Applied Optics, vol. 45. No. 14, May 10, 2006, pp. 3378-3381.

R. Lopez, et al., "Pulsed Laser Deposition of Conductive Metallo-Dielectric Optical Filters", Applied Physics, Dec. 20, 2011, pp. 307-310.

Mark Borek, et al., "Pulsed Laser Deposition of Oriented VO2 Thin Films on R-Cut Sapphire Substrates", Appl. Phys. Lett., Dec. 13, 1993, pp. 3288-3290.

R. Lopez, et al., "Enhanced Hysteresis in the Semiconductor-to-Metal Phase Transition of VO2 Precipitates Formed in SiO2 by Ion Implantation", Appl. Phys. Lett., vol. 79, No. 19, Nov, 5, 2001, pp. 3161-3163.

Y. Muraoka et al., "Metal-Insulator Transition of VO2 Thin Films Grown on TiO2 (001) and (110) Substrates", Appl. Phys. Lett., vol. 80, No. 4, Jan. 28, 2002, pp. 583-585.

G.I. Petrov et al., "Raman Microscopy Analysis of Phase Transformation Mechanisms in Vanadium Dioxide", Appl. Phys. Lett, vol. 81, No. 6, Aug. 5, 2002, pp. 1023-1025.

R. Lopez et al., "Switchable Reflectivity on Silicon from a Composite VO2-SiO2 Protecting Layer", Appl. Phys. Lett., vol. 85, No. 8, Aug. 23, 2004, pp. 1410-1412.

J. Rozen et al., "Two-Dimensional Current Percolation in Nanocrystalline Vanadium Dioxide Films", Appl. Phys. Lett, Feb. 2006, pp. 1-3.

J.Y. Suh, et al., "Modulated Optical Transmission of Subwavelength Hole Arrays in Metal-VO2 Films", Appl. Phys. Lett., Mar. 2006, pp. 1-3.

I. Karakurt, et al., "Transmission Increase Upon Switching of VO2 Thin Films on Microstructured Surfaces", Appl. Phys. Lett, Aug. 2007, pp. 1-3.

Bong-Jun Kim, et al., "Temperature Dependence of the First-Order Metal-Insulator Transition in VO2 and Programmable Critical Temperature Sensor", Appl. Phys. Lett., Jan. 2007, pp. 1-3.

J.S. Lee, et al., "Time-Resolved Visualization of the Heat Flow in VO2/Ai2O3 Films", Appl. Phy. Lett, Jan. 2007, pp. 1-3.

Gang Xu, et al., Thickness Dependence of Optical Properties of VO2 Thin Films Epitaxcially Grown on Sapphire (0 0 0 1), Applied Surface Science, Jan. 2005, pp. 449-452.

S. Lysenko, et al., "Light-Induced Ultrafast Phase Transitions in VO2 Thin Film", Applied Surface Science, Jan. 2006, pp. 5512-5515.

Jesse H. Day, "Thermochromism of Inorganic Compounds", Chemical Reviews, vol. 68, No. 6, Nov. 25, 1968, pp. 649-657.

Feliks Chudnovskiy, et al., "Switching Device Based on First-Order Metal-Insulator Transition Induced by External Electric Field", Wiley Interscience, 2002, pp. 1-8.

O. Ya. Berezina, et al., "Metal-Semiconductor Transition in Nonstoichiometric Vanadium Dioxide Films", Inorganic Materials, 2007, vol. 43, No. 5, pp. 505-511.

Changhong Chen, et al., "Micromachined Uncooled IR Bolometer Linear May Using Vo2 Thin Films", Int'l. Journal of Infrared and Millimeter Waves, vol. 22, No. 1, 2001, pp. 53-58.

Sihai Chen, et al., "Phase Transition VO2 Thin Films for Optical Switches", Int'l. Journal of Infrared and Millimeter Waves, vol. 25, No. 1, Jan. 2004, pp. 157-163.

P.J. Hood et al., "Millimeter-Wave Dielectric Properties of Epitaxial Vanadium Dioxide Thin Films", J. Appl. Phys. 70, Jul. 1, 1991, pp. 376-381.

Michael F. Becker, et al., "Femtosecond Laser Excitation Dynamics of the Semiconductor-Metal Phase Transition in VO2", J. Appl. Phys., Mar. 1, 1996, pp. 2404-2408.

J.H. Suh, et al., "Semiconductor to Metal Phase Transition in the Nucleation and Growth of VO2 Nanoparticles and Thin Films", Journal of Applied Physics, vol. 96, No. 2, Jul. 15, 2004, pp. 1209-1213.

S.A. Pauli, et al., "X-Ray Diffraction Studies of the Growth of Vanadium Dioxide Nanoparticles", Journal of Applied Physics, 2007, pp. 1-6.

A. Ilinski, et al., "Variations in Optical Reflectivity in the Semiconductor-Metal Phase Transition of Vanadium Dioxide", Journal of Non-Crystalline Solids, 2004, pp. 266-268.

J.Y. Suh, et al., "Modulation of the Gold Particle-Plasmon Resonance by the Metal-Semiconductor Transition of Vanadium Dioxide", Journal of Optics, 2008, pp. 1-6.

M. Soltani, et al., "Micro-Optical Switch Device Based on Semiconductor-to-Metallic Phase Transition Characteristics of W-doped VO2 Smart Coatings", J. Vac. Sci. Tech., Jul./Aug. 2007, pp. 971-975.

E. Cavanna, et al., "Optical Switching of Au-Doped VO2 Sol-Gel Films", Materials Research Bulletin, vol. 34, No. 2, 1999, pp. 167-177.

M. Maaza, et al., "Direct Production of Thermochromic VO2 Thin Film Coatings by Pulsed Laser Ablation", Elsevier, Optical Materials, 2000, pp. 41-45.

M. Maaza, et al., "Thermal Induced Tunability of Surface Plasmon Resonance in Au-VO2 Nano-Photonics", Elsevier, Optics Communications, 2005, pp. 188-195.

Hongchen Wang, et al., "Fabrication of VO2 Films with Low Transition Temperature for Optical Switching Applications", Elsevier, Optics Communications, 2005, pp. 305-309.

T. Ben-Messaoud, et al., "High Contrast Optical Switching in Vanadium Dioxide Thin Films", Elsevier, Optics Communications, 2008, pp. 1-4.

R. Lopez, et al., "Temperature-Controlled Surface Plasmon Resonance in VO2 Nanorods", Optics Letters, Aug. 1, 2002, vol. 27, No. 15, pp. 1327-1329.

G.I. Petrov, et al., "Nonlinear Optical Microscopy Analysis of Ultrafast Phase Transformation in Vanadium Dioxide", Optics Letters, Apr. 15, 2002, vol. 27, No. 8, pp. 655-657.

Matteo Rini, et al., "Photoinduced Phase Transition in VO2 Nanocrystals: Ultrafast Control of Surface-Plasmon Resonance", Optics Letters, vol. 30, No. 5, Mar. 1, 2005, pp. 558-560.

H.S. Choi, et al., "Mid-Infrared Properties of a VO2 Film Near the Metal-Insulator Transition", Physical Review, vol. 54, No. 7, Aug. 15, 1996, pp. 4621-4628.

R. Lopez, et al., "Size Effects in the Structural Phase Transition of VO2 Nanoparticles", Physical Review B, vol. 65, 200, pp. 1-5.

A. Cavalleri, et al., "Picosecond Soft X-Ray Absorption Measurement of the Photoinduced Insulator-to-Metal Transition in VO2", Physical Review, 2004, pp. 1-4.

A. Cavalleri, et al., "Evidence for a Structurally-Driven Insulator-to-Metal Transition in VO2: A View from the Ultrafast Timescale", Physical Review, 2004, pp. 1-4.

E.U. Donev, et al, "Optical Properties of Subwavelength Hole Arrays in Vanadium Dioxide Thin Films", Physical Review, 2006, pp. 1-4.

F.J. Morin, "Oxides Which Show a Metal-To-Insulator Transition at the Neel Temperature", Physical Review Letters, vol. 3, No. 1, Jul. 1, 1959, pp. 34-36.

A.S. Barker, et al., "Infrared Optical Properties of Vanadium Dioxide above and Below the Transition Temperature", Physical Review Letters, vol. 17, No. 26, Dec. 26, 1966, pp. 1286-1289.

Ramakant Srivastava et al., "Raman Spectrum of Semiconducting and Metallic VO2", Physical Review Letters, vol. 27, No. 11, Sep. 13, 1971, pp. 727-730.

A. Cavalleri, et al., "Femtosecond Structural Dynamics in VO2 During an Ultrafast Solid-Solid Phase Transition", Physical Review Letters, vol. 87, No. 23, Dec. 3, 2001, pp. 1-4.

R. Lopez, et al., "Size-Dependent Optical Properties of VO2 Nanoparticle Arrays", Physical Review Letters, vol. 93, No. 17, Oct. 22, 2004, pp. 1-4.

A. Cavalleri, et al., "Band-Selective Measurements of Electron Dynamics in VO2 Using Femtosecond Near-Edge X-Ray Absorption", Physical Review Letters, Aug. 5, 2005, pp. 1-4.

(56) References Cited

OTHER PUBLICATIONS

C. Kubler, et al, "Coherent Structural Dynamics and Electronic Correlations During an Ultrafast Insulator-to-Metal Phase Transition in VO2", Physical Review Letters, Sep. 14, 2007, pp. 1-4.

Jyrki Lappalainen, et al, "Microstructure Dependent Switching Properties of VO2 Thin Films", Elsevier, ScienceDirect, 2007, pp. 250-255.

Andriy Romanyuk, et al, "Temperature-Induced Metal-Semiconductor Transition in W-doped VO2 Films Studied by Photoelectron Spectroscopy", Elsevier, ScienceDirect, 2007, pp. 1831-1835.

B. Fisher et al., "The Metal-Semiconductor Transition Temperatures in Vanadium Oxides", Solid State Communications, vol. 33, 1979, pp. 965-967.

V.A. Klimov et al., "Hysteresis Loop Construction for the Metal-Semiconductor Phase Transition in Vanadium Dioxide Films", Solid-State Electronics, 2002, pp. 1134-1139.

E.V. Babkin, et al., "Metal-Insulator Phase Transition in VO2: Influence of Film Thickness and Subtrate", Electronics and Optics, 1987, pp. 11-14.

B. Felde, et al., "Plasmon Excitation in Vanadium Dioxide Films", Elsevier, Thin Solid Films, 1997, pp. 61-65.

P. Jin, et al., "Tungsten Doping into Vanadium Dioxide Thermochromic Films by High-Energy Ion Implantation and Thermal Annealing", Elsevier, Thin Solid Films, 1998, pp. 151-158.

Ningyi Yuan, et al., "The Large Modification of Phase Transition Characteristics of VO2 Films on SiO2/Si Substrates", Elsevier, ScienceDirect, 2006, pp. 1275-1279.

Yan Jiazhen, et al., "Effect of Mo-W Co-doping on Semiconductor-Metal Phase Transition Temperature of Vanadium Dioxide Film", Elsevier, ScienceDirect, 2008, pp. 8554-8558.

Justyna K. Ganel, et al., "Gold Helix Photonoic Metamaterial as Broadband Circular Polarizer", Science AAAS, vol. 325, 2009, pp. 1513-1515.

T. Driscoll, et al., "Memory Metamaterials", Science AAAS, vol. 325, 2009, pp. 1518-1521.

\* cited by examiner

OPTICAL SENSORS INCLUDING SURFACE MODIFIED PHASE-CHANGE MATERIALS FOR DETECTION OF CHEMICAL, BIOLOGICAL AND EXPLOSIVE COMPOUNDS

BACKGROUND

The ability to detect chemical and biological substances in the field, particularly in military and other related operations, has become increasingly important. In particular, rapid detection and identification of certain explosive or dangerous chemical and biological agents utilizing a device that is automated, preferably portable and capable of detecting threats in real time with minimal sample collection is highly desirable.

The detection of chemical compounds (for illustrative purposes: organophosphates) are of particular interest, since many chemical warfare nerve agents as well as highly toxic pesticides include such compounds. Examples include, without limitation, sarin (O-isopropyl methylphosphonofluoridate), VX (O-ethyl S-[2-(diisopropylamino)ethyl]methylphosphonothioate), Parathion (O,O-Diethyl-O-4-nitrophenylthiophosphate), and Chlorpyrifos (O,O-diethyl O-3,5,6-trichloro-2-pyridyl phosphorothioate). Likewise, explosive compounds (which are predominately nitro-aromatic chemicals) and biological warfare agents pose severe risks to warfighter and civilian populations.

It is desirable to provide a sensor that easily and accurately determines the presence of chemical, biological or explosive compounds such as any of the above-identified compounds, even at small concentrations, within such environments that civilians and warfighters will/must exist.

SUMMARY

In accordance with an embodiment of the present invention, a sensor device comprises an optical limiting structure comprising a metal layer including at least one metal particle having a size no greater than about 1500 nanometers, and a phase-change material layer disposed adjacent at least a portion of the metal layer, the phase-change material layer comprising a phase-change material, and a dendritic-metal layer disposed over at least a portion of the phase-change material layer of the optical limiting structure, the dendritic-metal layer comprising an organic compound including branching chain amino acid groups attached to a metal structure. The optical limiting structure is configured to transition from a first optical state to a second optical state when the phase-change material is heated above a critical temperature, with transmittance of light at a predetermined wavelength through the optical limiting structure being lower at the second optical state of the optical limiting structure in relation to the first optical state of the optical limiting structure.

In accordance with another embodiment of the invention, a method of detecting the presence of chemical, biological and explosive materials with an optical sensor device is provided, the sensor device comprising an optical limiting structure including a metal layer with at least one metal particle having a size no greater than about 1500 nanometers, and a phase-change material layer that includes a phase-change material and that is disposed adjacent at least a portion of the metal layer, and a dendritic-metal layer disposed over at least a portion of the phase-change material layer of the optical limiting structure, the dendritic-metal layer including an organic compound including branching chain amino acid groups attached to a metal structure. The method comprises capturing and decomposing a phosphorus-containing organic compound via the dendritic-metal layer, wherein the decomposition of the phosphorus-containing organic compound captured by the dendritic-metal layer initiates a transition of the optical limiting structure from a first optical state to a second optical state, and detecting a transition of the optical limiting structure from the first optical state to the second optical state.

The present invention facilitates rapid and reliable detection by a device (e.g., a portable device) of chemical, biological and explosive materials, such as dangerous phosphorous-containing organic compounds (including organophosphate compounds such as sarin and VX).

The above and still further features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION

The present invention relates to utilizing a nanostructured sensor configuration in which explosive, chemical and/or biological compounds are detected by the enthalpy change or heat released due to a decomposition reaction that takes place at a surface location of the sensor, where the released heat results in a detectable optical response of the sensor.

It is known that certain phase-change materials have the ability to change colors and/or to reflect, block, or limit the transmittance of light at different wavelengths based upon changes in temperature and/or light absorbed by the phase-change materials. This facilitates the use of certain phase-change materials for use in applications such as light blocking or filtering applications.

In addition, it is known that the combination of certain phase-change materials having thermochromic and/or photochromic properties, when formed as thin films over arrays of noble metal nanoparticles, can result in a defined or designated profile in the surface-plasmon resonance (SPR) such that optical extinction (i.e., the ability to substantially limit or block the transmittance of light at one or more wavelengths) through the combined phase-change material/metal nanoparticle layers can be shifted by as much as tens of nanometers.

In accordance with the present invention, an optical sensor comprises a phase-change material layer disposed over at least a portion of a metal particle layer, and a branching or dendritic-metal structure layer disposed over the phase-change material layer.

The dendritic-metal structure layer includes an organic compound that captures a target material of interest and decomposes the target material. For example, the dendritic-metal structure layer can include amine functional groups that are designed to mimic an enzyme such as organophosphorous hydrolase, where the branching or dendritic amine functional groups extending from the central or core location of the dendritic-metal structure layer define empty spaces or "pockets" which facilitate the capture, hydrolysis and decomposition of phosphorous-containing or phospho-organic compounds (such as organophosphates) that come in proximity with the dendritic-metal structural layer. The enthalpy change or heat released from the decomposition of the target material (such as phospho-organic compounds) captured by the dendritic-metal structure layer causes a resultant change and surface-plasmon resonance (SPR) shift in the optical properties of the underlying phase-change material/metal particle layers, which results in a detection and identification of the target material by the optical sensor.

The phase-change material layer can be formed with one or more thermochromic materials and/or one or more photochromic materials (i.e., one or more thermochromic materials, one or more photochromic materials, or combinations of one or more thermochromic materials and one or more photochromic materials).

In an example embodiment, the phase-change material utilized to form the phase-changing material layer is vanadium oxide, which is a thermochromic material and refers to a number of different forms of vanadium oxides including, without limitation, $VO_2$ and $V_2O_3$. However, the present invention is not limited to the use of vanadium oxides but instead can be formed from any one or combination of phase-change materials which undergo optical property changes when subjected to temperature or light changes so as to block or substantially limit transmittance of light at one or more selected wavelengths through the phase-change material layer.

Thermochromic materials undergo phase transitions upon being heated above a critical temperature. For example, vanadium dioxide ($VO_2$) undergoes a phase transition from a semiconductor state to a metal state upon being heated to a temperature above about 68° C. In particular, vanadium dioxide, $VO_2$, undergoes a reversible transition from a semiconductor phase (where the $VO_2$ has a monoclinic crystal structure) to a metal phase (where the $VO_2$ has a tetragonal crystal structure) at a critical temperature of about 68° C. The transitional phase change at this critical temperature results in the $VO_2$ exhibiting a rapid change in electrical and optical properties. At this temperature-induced phase transition, $VO_2$ acts as an optical "blocker" or barrier that substantially limits the transmittance of light to achieve optical extinction at near-infrared (near-IR) wavelengths of about 1.2 micrometers.

Examples of other suitable thermochromic materials that can be used to form the phase-change material layer include, without limitation, metal oxide-based materials such as $Ti_2O_3$, $NiS_{2-y}Se_y$, $LaCoO_3$, $PrNiO_3$, $Cd_2Os_2O_7$, $NdNiO_3$, $Tl_2Ru_2O_7$, $NiS$, $BaCo_{1-y}Ni_yS_2$, $Ca_{1-y}Sr_yVO_3$, $PrRu_4P_{12}$, $BaVS_3$, $EuB_6$, $Fe_3O_4$, $La_{1-y}Ca_yMnO_3$, $La_{2-2y}Sr_{1+2y}Mn_2O_7$, $Ti_4O_7$ and $La_2NiO_4$ and any combinations of these compounds (where $y \leq 1$). Other suitable thermochromic materials that can be used to form the phase-change material layer are polymers including, without limitation, azobenzene-containing polydiacetylenes, polyvinylidene fluoride, polyvinyl acetate, polyvinyl phenylene, polystyrene sulfonate, and polyanilines (e.g., polyanilines doped into synthetic opal nanostructures). Still other suitable materials may be nanostructured polymers, such as diblock (poly[styrene-b-isoprene] or PS-b-PI) and triblock (the rod-coil copolymer poly[poly(N-isopropylacrylamide)-b-polyfluorene-b-poly(N-isopropylacrylamide)]) copolymers.

The metal layer can be formed from at least one nanosized particle. Preferably, the metal layer is formed with a plurality of nanosized metal particles, where the metal particles comprise nanosized structures having cross-sectional dimensions (e.g., length, width, thickness and/or diameter dimensions) on the order of no greater than about 1500 nanometers (nm), preferably no greater than about 1000 nm, or no greater than about 500 nm, and more preferably no greater than about 300 nm. In a preferred embodiment, the metal particles can have cross-sectional dimensions ranging from about 20 nm to about 250 nm. The metal particles are arranged in a pattern or array defining the metal layer, and a film or thin layer of the phase-change material is formed over the array of metal particles as described below. Suitable metals that can be used to form the metal layer include, without limitation, noble metals such as gold, platinum, palladium and silver, base metals such as copper and aluminum, and any combinations, alloys (e.g., a gold/silver alloy, a gold/copper alloy, etc.), and/or oxides (e.g., silver oxide) of such metals. The term "metal particle", as generally used herein and unless specified otherwise, refers to a structure including at least one of a metal, an oxide of the metal and an alloy of the metal.

Any suitable process can be utilized to form a selected pattern or array of metal particles on a substrate during formation of the sensor device of the invention. For example, photolithography techniques can be used to form a channeled pattern of voids within a resist, followed by deposition of the metal within the channeled pattern of voids and removal of the resist. Techniques such as focused ion beam (FIB) lithography and electron beam (EB) lithography are particularly useful, since such techniques facilitate the formation of any selected pattern with a high level of accuracy and precision. Alternatively, any other suitable process, such as a stamping, self-assembling, colloid-mask lithography or imprinting process, can also be used to form an array of nanosized metal particles. As described in further detail below, different arrays of nanosized particles can be provided in which the nanosized particles have a variety of different geometric shapes, dimensions, spacings, and/or orientations to form structures capable of blocking, reflecting, absorbing or substantially limiting transmittance of light through the structures at a variety of different wavelength ranges.

The metal layer comprising the array of nanosized metal particles is at least partially covered by a thin film layer of the phase-change material. The phase-change material can be deposited over the metal particles in any suitable manner, such as by chemical vapor deposition or physical vapor deposition (e.g., pulsed laser deposition). Preferably, the phase-change material layer or film is formed having a thickness no greater than about 100 nm. For example, a thin film of the phase-change material can be formed over an array of metal particles using a pulsed laser deposition (PLD) or other similar process having a thickness in the range from about 10 nm to about 50 nm.

The combined phase-change material and metal particle layers of the sensor device can be formed with any selected combinations of metal layers and/or phase-change material layers. In one example, an optical limiting structure for the sensor device can be formed with a phase-change material layer disposed over a metal layer comprising an array of metal nanoparticles. In another example, an optical limiting structure can be formed with a metal layer disposed over a phase-change material layer. In a further example, an optical limiting structure can be formed with a metal layer comprising an array of metal nanoparticles disposed or "sandwiched" between two films or layers of phase-change material, where each phase-change material layer can include the same or different one or combination of phase-change materials (i.e., thermochromic and/or photochromic materials). In still another example, the phase-change material can be formed over surface portions of nanosized metal particles, where the spaces between metal particles remain uncovered by the phase-change material such that a series of phase-change material layers are formed either over individual particles (so as to form a "hat" or partial covering over a portion of each metal particle) or over sets of particles with uncovered spaces remaining between the covered particles or the sets of covered particles.

Thermochromic materials used to form the phase-change material layer can be provided with any one or combination of suitable dopants. Certain dopants can be provided within the thermochromic material to effect a shift or change in the critical temperature at which the thermochromic material transitions so as to block or limit transmittance of light at one or more selected wavelengths through the phase-change material layer. For example, dopants such as tungsten and chromium can be added to vanadium dioxide to change (e.g., lower) its critical phase transition temperature to temperatures as low or even lower than room temperature (about 27° C.), which enhances the applications and environments in which vanadium dioxide may be used as an optical "blocker" or barrier of light at certain wavelengths. Other dopants can influence the transmissivity and/or other optical properties of the phase-change material. Examples of suitable dopants include, without limitation, tungsten, fluorine, titanium, chromium, and combinations thereof, where the dopant or combinations of dopants are provided within the thermochromic material at concentrations ranging from about 0.05 atomic % to about 5 atomic %.

The formation of a series of two or more layers comprising at least one phase-change material layer formed over a metal layer comprising an array of nanosized metal particles results in a structure that shifts the wavelength range at which the structure is capable of blocking, reflecting, absorbing or substantially limiting the transmittance of light in relation to the wavelength (or range of wavelengths) at which the phase-change material layer by itself is capable of substantially limiting the transmittance of light. As used herein, substantially limiting the transmittance of light through a structure including a phase-change material refers to the structure having certain optical properties (e.g., due to a phase transition of the phase-change material within the structure) such that the structure limits the transmittance of light at a specified wavelength through the structure to a value of no greater than about one part in one million (i.e., an optical density of at least about 6). Transmittance is defined herein as follows: (intensity of light emerging from the structure at the specified wavelength)/(intensity of the incident light directed toward the structure at the specified wavelength). The substantial limiting of light of a particular wavelength or range of wavelengths can be determined, for example, by measured optical extinction spectra (representing the extinction of transmittance through the structure) as a function of wavelength, where a peak in the optical extinction data plotted vs. wavelength represents the wavelength range at which the structure substantially limits the transmittance of light.

A wavelength or wavelength range at which the combined phase-change and metal particle layered structure can block or substantially limit the transmittance of light can be shifted (e.g., blue-shifted, which refers to a shortening of the wavelength) in the region of the spectrum bounded from about 250 nm to about 2500 nm.

For example, as noted above, $VO_2$ is capable of substantially limiting the transmittance of near-IR light at a wavelength in the range of about 1200 nm (1.2 μm) upon being heated above a critical temperature of about 68° C. (which is the point at which $VO_2$ transitions between semiconductor and metal states) with no doping of the $VO_2$. In accordance with the present invention, an optical limiting structure for the sensor device can be formed including a thin film or layer of $VO_2$ deposited over an array of nanosized metal particles (e.g., gold particles or any other one or combination of metals as described above) in which the structure is capable of substantially limiting the transmittance of light at blue-shifted wavelengths shorter or less than 1200 nm when the $VO_2$ transitions from a semiconductor state to a metal state, including the limiting of the transmittance of light in the visible range (e.g., wavelengths in the range from about 400 to about 800 nm) and even in the near-ultraviolet range (e.g., wavelengths lower than about 400 nm). For example, using an array of round or circular shaped gold particles and a $VO_2$ layer deposited over the metal layer, a resultant structure can be formed that substantially limits the transmittance of light through the structure at wavelengths shifted by at least about 150 nm from 1200 nm.

The combination of the surface plasmon resonance that is generated by the nanosized metal particles forming the metal layer with the physical properties of the phase-change material layer that covers and that is adjacent or in close proximity (within about 20 nm) in relation to the metal particle layer results in a wavelength "tuning" at which the transmittance of light is effectively blocked or substantially limited (i.e., optical extinction) through an optical limiting structure formed by the combination of the metal and phase-change material layers. Therefore, an optical limiting structure for the sensor device of the present invention can be formed that includes a phase-change material such as $VO_2$ (which typically is capable of blocking, reflecting, absorbing or substantially limiting the transmittance of light in the near-IR range) in which the light blocking capabilities of the structure are blue-shifted (e.g., to the visible and/or UV wavelength ranges, such as a shift to the green light spectrum and/or the blue light spectrum) based upon the light blocking requirements for a particular application.

A number of factors can control the wavelength "tuning" for blocking, reflecting, absorbing or substantially limiting transmittance of light by the optical limiting structure. Examples of such factors which can control such a shift in wavelength and resultant ability of the optical limiting structure to block or substantially limit transmittance of light include, without limitation, selection of one or more combinations of different phase-change materials and/or one or more different metals used to form the layered structure, size and arrangement of metal particles within the array forming the metal layer, thickness of the phase-change material layer(s), arrangement of arrays within arrays of particles, arrangement of particles having varying shapes and sizes within arrays, and number/variety of phase-change and/or metal layers used to form the layered structure. Thus, optical limiting devices can be formed in accordance with the invention that are tailored to blocking, reflecting, absorbing or substantially limiting transmittance of light of different wavelengths based upon the requirements or specifications in which the devices are to be used.

Upon forming the composite of the phase-change material layer with metal particle layer, a branching or dendritic-metal structure layer can be formed over the phase-change material layer. The dendritic-metal structure layer provides a surface for the sensor that captures and decomposes target materials or compounds of interest, such as phosphorus-containing organic (phosphor-organic) molecules. The decomposition of the target material results in heating of the underlying phase-change material layer above its critical temperature so as to change the optical properties of the sensor device. The change in optical properties of the sensor device can be detected by the sensor to provide an indication of the presence of the target material or compound in the ambient surroundings in which the sensor is located.

The dendritic-metal structure layer includes an organic compound with branching amine functional groups extending from the central or core location of the dendritic-metal structure layer to define empty spaces or "pockets" which facilitate the capture, hydrolysis and decomposition of target materials such as phosphor-organic compounds that come in proximity with the dendritic-metal structure layer. For example, the dendritic-metal structure layer can be designed to mimic the functionality of an enzyme such as organophosphorus hydrolase (OPH). Organophosphorus hydrolase is an important enzyme that, via a catalytic reaction, hydrolyzes and decomposes organophosphate (OP) compounds including many pesticides and nerve agents such as VX, sarin and Chlorpyrifos. However, the use of OPH for decomposition of OP compounds is undesirable due to the short shelf-life and expensive costs associated with production of this enzymatic catalyst. An alternative approach is to synthesize in a more cost effective manner substitute organic amine compounds that can mimic the functionality of OPH and which have sufficient stability.

Dendritic organic structures (also referred to as dendrimers or dendrons) can be formed including a pyridinyldithio functional group at focal points of the structures which facilitate attachment with metal nanoparticles. The synthesis of an example dendron unit featuring pyridinyldithio functionality at its focal point is described in Scheme 1 shown below:

SCHEME 1:

A nitrotriester monomer 1 is hydrogenated with Raney-Nickel catalyst to form an aminetriester monomer 2. The synthesis of the dendron scaffold is initiated by reacting a nitrotriacid monomer 3 with monomer 2 so as to form the resulting dendron 4. The dendron 4 is hydrogenated with Raney nickel catalyst to reduce the nitro group at the core of the dendron to an amine group. The resultante amine dendron 5 is then reacted with 3-(2-pyridinyldithio)propanoic acid via amide coupling reaction and the t-butyl ester groups on the resulting product are subsequently deprotected with formic acid to yield dendron product 7. The resultant dendron product 7 with the disulfide linker attached to the focal point can undergo a thiol-disulfide exchange with a cargo molecule that has a sulfhydryl functionality or the disulfide can be cleaved to reveal a sulfhydryl functionality that can cleanly react with a metal or metal oxide surface (such as gold or other noble metals, or metal oxides such as titanium dioxide) in a self-assembly chemisorption to form a dendritic-metal structure that can be attached with the phase-change material layer to form the sensor of the invention. The amide backbone is very stable toward different pH conditions and is suitable to complex with metal ions, such as copper and zinc, to provide the pockets for a catalytical reaction with a target compound of interest.

To further advance the dendrimer backbone, free amine groups can be integrated with the backbone of the dendron to promote the complexation with metal ions. In particular, lysine (Lys) and/or histidine (His) units can be added to the dendron. The lysine will offer a free amine group whereas a histidine amino acid provides an imidazol unit for the enhanced complexation with metal ions. The following two schemes shown below provide examples of integrating amino acid units into the dendron. In particular, Scheme 2 shows an example of integrating lysine units into a dendron structure (compounds 13 and 14 in Scheme 2), while Scheme 3 shows an example of starting with dendron structure 8 formed in Scheme 2 and forming a dendron structure including histidine units (compounds 17 and 18 in Scheme 3).

SCHEME 2:

13

14

SCHEME 3:

-continued

18

It is also possible to incorporate other combinations of amino acid units into the dendron structure including, without limitation, cysteine (Cys) and isoleucine (Ile), in order to closely match the binding pocket of a native enzyme. For OPHs, at least some of these binding pocket domains are believed to include His-X-His-X-Cys, Cys-Ile-X-His-Ser, and His-Ile-X-His-Ser, where X represents an uninvolved (random) amino acid.

The dendrons formed as described above include thiol groups at the focal point of the structure which can be used to attach the dendron structures to metal structures, such as metal particles, metal films or layers, or any other suitable forms and types of metal structures. Suitable metals that can be used to bind with the dendron structures include, without limitation, noble metals such as gold, platinum, palladium and silver, or other metals such as titanium, copper, zinc and aluminum. In addition, certain metal oxides can also be used including, without limitation, aluminum oxide, zinc oxide, and titanium dioxide. In an example embodiment metal particles such as gold particles are used to bind with the dendron structures. The metal particles may optionally be in dimensionally different structures, such as particles, disks, rods, spirals and/or combinations of such structures.

In an example embodiment, a disulfide linker of a dendron structure such as the structure 7 shown in Scheme 1 can be cleaved with DTT (dithiothreitol) and reacted with $HAuCl_4$ in a mixture of MeOH/AcOH 6:1 and stirred at $-70°$ C. The reaction mixture can be warmed from about $-10°$ C. to about $0°$ C. and reduced with $NaBH_4$ to form a precipitate of the dendritic-metal structure, which can be formed into particles, a film or any other suitable structure.

After the dendritic-metal structure is formed, a catalytic metal structure is provided in proximity with the dendron structure which catalyzes the decomposition of the target compound of interest.

For example, the peptide spaces or "pockets" in the dendron structure can be complexed with metal ions to form the catalytic active sites within the pockets. Open coordination sites on the metal ions within the peptide pockets of the dendron can coordinate with water to activate an H—OH bond which then carries out the hydrolase function of adding water across a target molecule's bond. For organophosphate (OP) molecules, it is often the P—O (phosphorus-oxygen) bond which is broken during hydrolysis and decomposition of the OP molecule. However, the dendritic-metal structure can also target a P—F (phosphorus-flourine) bond, a P—CN (phosphorus-cyano) bond and a P—S (phosphorus-sulfur) bond of other phospho-organic compounds for hydrolysis and decomposition of compounds including such bonds.

The dendron structure can be complexed with metal ions to form a bimetallic center including a suitable metal ion, such as zinc or cobalt. For example, a Zn and/or Co metal center within a dendron pocket helps activate a water molecule to prepare the H—OH bond for breaking a phosphorus bond such as P—O, P—F, P—CN or P—S. As noted above, the breaking of this bond results in an enthalpy change with a release of heat. The selection of certain metal ions that are to be bound to specific site locations within the dendron pockets can be controlled by titrating in a first type of metal ion (such as Zn2+) so that it reacts with strongest binding sites first, and then adding a second type of metal ion (such as Co2+) to fill the remaining coordination sites within the pockets. For example, the second metal can be coordinated to a secondary amine of the peptide that helps with creating the hydrogen bonding necessary in the enzymatic pocket. For OPHs, these peptide domains for the Zn active site may include His-X-His-X-Cys, Cys-Ile-X-His-Ser, and His-Ile-X-His-Ser where X is an uninvolved (i.e., random) amino acid. In mimicking wild-type OPH active sites, four suitable choices for metal ions that can be complexed with the dendron structure are Zn2+, Co2+, and Cd2+.

Alternatively, the metal or metal oxide layer to which the dendron structure attaches can serve as a catalyst for certain target compounds of interest. For example, the dendritic-metal structure can comprise titanium dioxide ($TiO_2$) which serves as a binding structure for the dendrons as well as a catalyst for certain target compounds. In this embodiment, the dendron pockets capture the target compound of interest, and the titanium dioxide to which the dendron structures are attached catalyzes the decomposition of the captured target compound, resulting in a release of heat which is detected by the underlying optical limiting layer.

It is further noted that the size of the dendritic-metal structure can be controlled by controlling the size of the internal metal core according to any number of known methods (e.g., synthetic reaction control of the metal core size). Thus, dendritic-metal particles can be formed of any suitable dimensions (e.g., diameters), or dentritic-metal layers can be formed of any suitable thicknesses.

The dendritic-metal structure can be attached to the phase-change material/metal particle layers (or to an underlying catalytic metal layer) in any suitable manner. For embodiments in which the dendritic-metal structure is attached to the phase-change material layer, the combined dendritic-metal structure can first be formed and then applied to the phase-change material layer or, alternatively, nanosized metal particles can be applied to the phase-change material layer followed by binding the dendron structures to the nanosized metal particles (e.g., via a thiol bond as described above). For example, nanosized metal particles can be lithographically patterned onto the phase-change material layer (e.g., using electron-beam lithography). Alternatively, preformed nanosized metal particles can be bound to the phase-change material layer (e.g., using thiol assembly chemistries similar to those described above for binding the dendron structures to the metal particles). Nanosized metal particles can be formed in a size range from about 1 nm to about 5 nm if preformed in solution and then applied to the phase-change material layer. Nanosized metal particles can also be formed in a size range from about 10 nm to about 300 nm when using electron-beam lithography to form the particles directly on the phase-change material layer. Dendritic-metal structures can be formed with the nanosized metal particles solution, or applied as a separate thiol functionalized (sulfur linker) layer when applied to bare nanosized metal particles formed by lithography over the phase-change material layer.

The overall sensor thickness can include a 1-1000 nm thick optical layer comprising the phase-change material layer, and 1-1000 nm metal layer comprising the dendritic-metal structures.

An example embodiment of forming an optical sensor device is now described with reference to FIGS. 1-7. In this example, an optical limiting structure is first formed, where a $VO_2$ layer covers a metal layer comprising an array of nanosized gold particles. However, it is noted that the formation techniques described herein are also applicable to forming other optical limiting structures using different phase-change materials and/or different metals, as well as different dendritic-metal structural layers.

Figure 1:
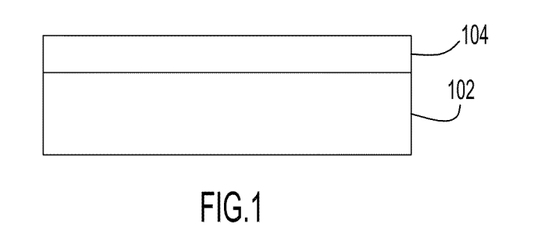
FIGS. 1-7 schematically depict the formation of an optical sensor in accordance with the present invention.

Referring to FIG. 1, a substrate is provided including a glass layer 102 with an indium tin oxide (ITO) layer 104 formed over the glass layer 102. Alternatively, it is noted that any other suitable substrate layer may also be provided for forming the metal particle array. The ITO layer can be about 10 nm to about 20 nm in thickness and provides a thin conductive layer for the lithography process. A focused ion beam (FIB) lithography process is used to form an array of nanosized gold particles on the substrate. In particular, the FIB lithography is performed using a FEI/Philips FIB200 focused ion beam (FIB) writer, based on a liquid $Ga^+$ ion source operating at 30 kV. A software interface of the FIB facilitates the input of a variety of different lithographic patterns and control of ion-beam current on a pixel-by-pixel basis.

Figure 2:
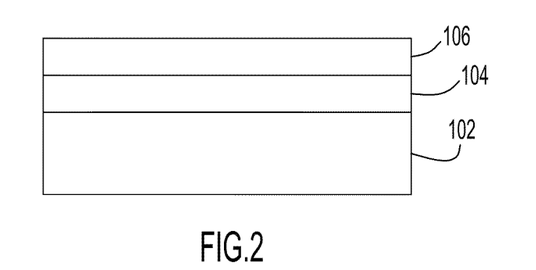

A solution of poly-(methyl methacrylate) (PMMA; standard molecular weight 950 K) in anisole (1.7 wt %) is spun onto the substrate including glass layer 102 and ITO layer 104 in two consecutive stages (first at 500 rpm for about 5 seconds, then at 4000 rpm for about 45 seconds) and heated on a hot plate at about 180° C. for 1 minute to obtain a PMMA layer 106 having a uniform thickness of about 50 nm to about 60 nm (FIG. 2). Preferably, the thickness of the PMMA layer is chosen to be at least three times the desired thickness of the nanosized metal particle layer in order to achieve a high quality lift-off of the PMMA layer after the formation of the metal layer. The $Ga^+$ beam is focused to a nominal beam diameter of 8 nm to create the pattern of pixel dot arrays on the PMMA (e.g., beam current can be set at 1 pA, and dwell time per dot can be 80 μs).

Figure 3:
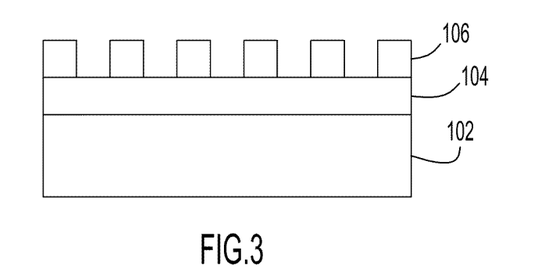
Figure 4:
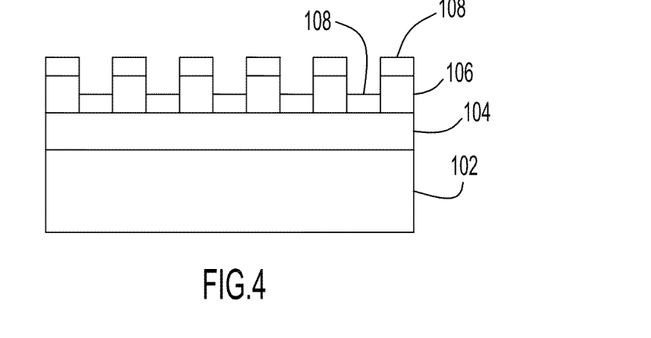
Figure 5:
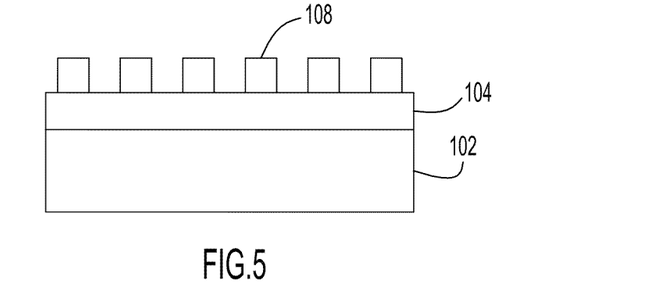

The exposed PMMA is developed in a 1:3 methyl isobutyl ketone and isopropyl alcohol mixture and the irradiated portions of the PMMA layer 106 are then removed, leaving a PMMA patterned resist structure 6 on the substrate (FIG. 3). A gold layer 108 is then deposited (e.g., using a conventional or other suitable physical vapor deposition techniques) over the PMMA patterned structure 106 (FIG. 4). The gold layer can be deposited with a uniform thickness of about 20 nm. After deposition of the gold layer 108, the PMMA resist structure 106 is removed using any conventional or other suitable "lift-off" procedure using a commercially available solvent. This results in the remaining metal layer 108 comprising nanosized gold particles arranged in a desired array and having suitable spacings, dimensions and geometric shapes (FIG. 5).

Using focused-ion-beam (FIB: 30-keV $Ga^+$) lithography in a PMMA mask (e.g., 60 nm thick), followed by vapor deposition of gold (e.g., about a 20 nm thickness) and conventional or other suitable lift-off techniques, arrays of gold nanosized particles of various sizes and shapes can be formed including, without limitations, round and/or ellipsoidal (e.g., 3:1 aspect ratio) cylindrical disk structures, multi-faceted structures (e.g., square, rectangular structures, or other polygon shaped structures), spiral shaped structures, irregular and/or asymmetrical shaped structures, etc. Thus, a variety of arrays of metal particles having varying sizes and shapes can be formed using this process. As noted above, metal particles can be formed having cross-sectional dimensions in the range from about 20 nm to about 250 nm.

A similar process for forming a nanosized metal particle array using a PMMA mask can be achieved with electron-beam lithography, although the interaction of electrons with the photoresist (PMMA) is different. Electrons are capable of penetrating deeper into the PMMA resist than the $Ga^+$ ions in the FIB lithography process, thus requiring more electrons to achieve proper exposure but increasing resolution considerably in relation to FIB lithography. Particle shapes and sizes can therefore be more reproducible and better controlled using electron-beam lithography, allowing for a more precise or fine tuning of the optical properties of the layered optical limiting structure. The resist parameters (e.g., PMMA thickness and development times) used for electron-beam lithography are substantially similar to that of FIB lithography. Example beam currents that can be used for electron-beam lithography are approximately 11 pA with an area dosage of 100 μC/cm$^2$ at 10 kV. Dosage and accelerating voltage requirements depend on the resist thickness and desired resolution. In addition, for mass production, a mask or masks can be made by electron-beam lithography, and then used in other template-based schemes, such as nanoimprint lithography, to permit rapid mass production of substrates of any particular design.

Figure 6:
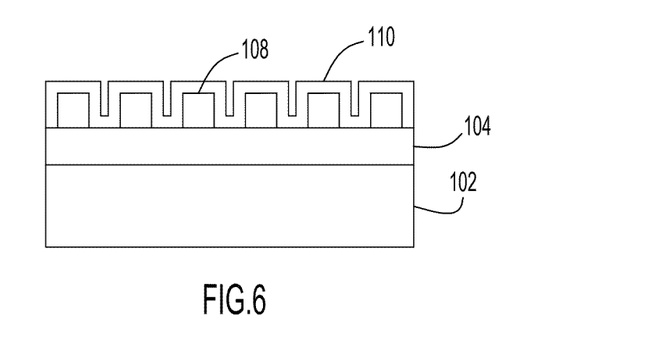

A VO$_2$ layer 110 is formed over the metal layer 108 comprising the array of nanosized gold particles by pulsed-laser deposition followed by thermal oxidation of the deposited layer (FIG. 6). First, a beam from a KrF excimer laser ($\lambda$=248 nm) is focused onto a vanadium target at a fluence of about 4 J/cm$^2$ to deposit a sub-stoichiometric vanadium oxide (VO$_{-1.7}$). The sample is then annealed at 450° C. under 250 mTorr of oxygen gas for about 40 minutes to convert the amorphous film into stoichiometric, crystalline VO$_2$. The formed VO$_2$ layer 110 has a thickness of about 50 nm. However, the pulsed-laser deposition process can be controlled so as to form the VO$_2$ layer having any desired thickness (preferably within the range from about 10 nm to about 50 nm). In addition, the VO$_2$ layer can be doped with any one or combination of the previously noted dopants so as to lower the critical temperature at which the VO$_2$ layer reversibly transitions to having different optical properties. While the VO$_2$ layer shown in FIG. 6 is disposed substantially entirely over the metal layer, it is noted that the VO$_2$ layer can alternatively be formed over only portions of the metal layer or even over individual metal particles in the array (e.g., to form a "hat" or partial covering over individual metal particles), while leaving portions of the array exposed (i.e., not covered by the VO$_2$ layer).

Figure 7:
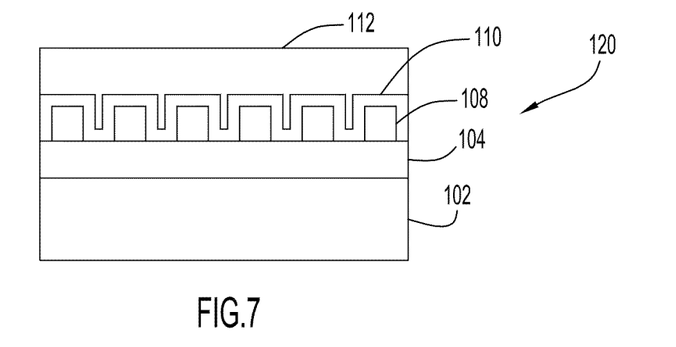

Referring to FIG. 7, a dendritic-metal structure (e.g., including catalytic metal ions complexed within pockets of the branching peptide chains or, alternatively, including a metal or metal oxide within the structure that serves as a catalyst for a target compound of interest) is formed in the manner described above, and this dendritic-metal structure is further applied to form a layer 112 over the VO$_2$ layer 110, which results in an optical sensor 120. As noted above, the dendritic-metal structure can be formed by first applying the nanosized metal particles to the phase-change material layer by lithography, followed by attachment of the dendron structures to the metal nanoparticles. Alternatively, the dendritic-metal structures can be formed together and then applied to the phase-change material layer.

Figure 8:
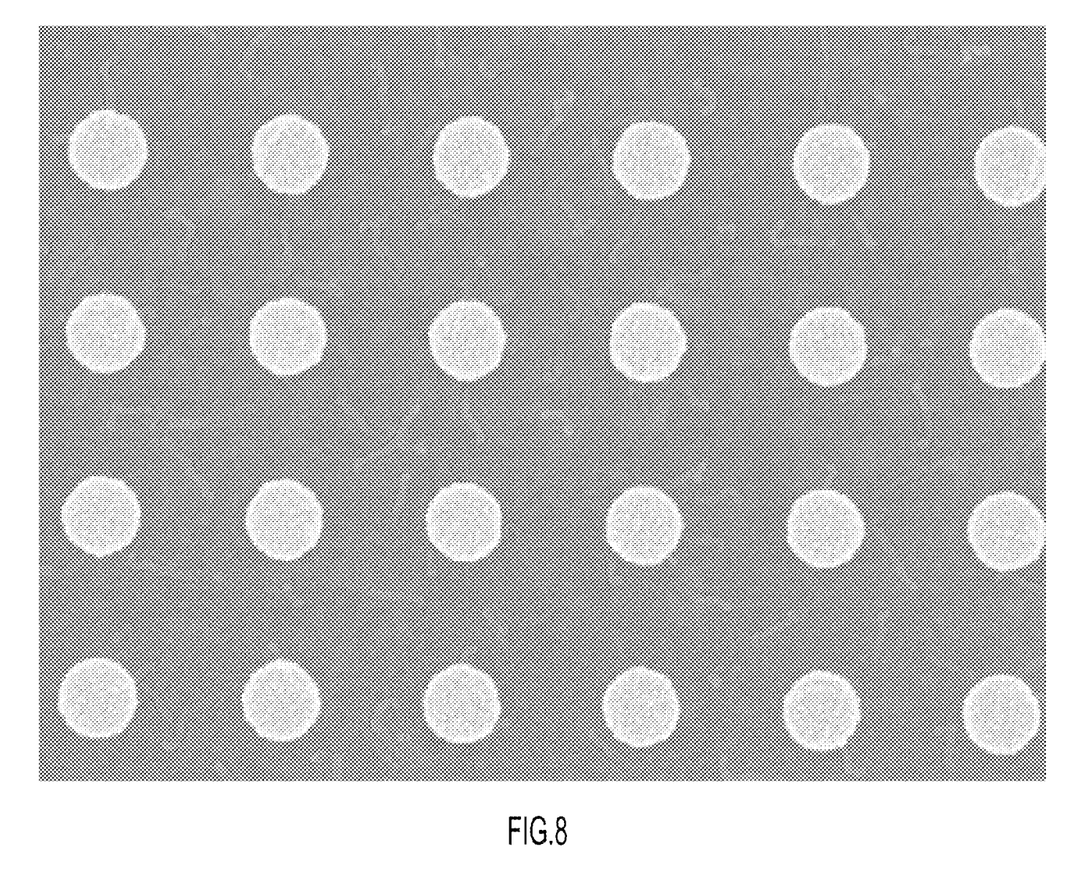
FIG. 8 is a scanning electron micrograph image of an example array of nanosized metal particles that can be used to form the metal layer of an optical sensor structure in accordance with the present invention.

The arrangement, size and geometric shapes of the nanosized metal particles in the optical limiting structure array have an effect on the wavelength "tuning" of the optical limiting structure for the optical sensor (i.e., tuning of the wavelength range in which optical extinction occurs due to the phase transition of the phase-change material). An example array of gold nanoparticles which can be used in forming the optical limiting structure for the optical sensor is shown in the scanning-electron micrograph (SEMs) of FIG. 8, where the gold particles of the array are round and substantially uniform in size (e.g., having a diameter of about 188 nm) and substantially uniformly spaced from neighboring particles (e.g., with distances between neighboring particles being about 267 nm).

A wide variety of different arrays of nanosized metal particles can also be formed. Examples of such different arrays of metal particles are described in co-pending U.S. patent application Ser. No. 12/479,311, the disclosure of which is incorporated herein by reference in its entirety.

The sensor device can be provided with any suitable structure or mechanism that is capable of detection of a transition of the optical limiting structure between different optical states when the phase-change material is heated above its critical temperature. In one example shown in FIG. 9, the sensor device 120 is provided with a light source 122 and a detector 124 (e.g., a charge coupled device) disposed at opposing sides of sensor device, where the light source 122 projects light at one or more selected wavelengths toward the sensor device and the detector 124 is positioned near an opposing side of the sensor device to detect the transmittance of light from the light source 122 through the sensor device. For example, the detector 124 can be configured to detect and measure the amount or intensity of light at the one or more selected wavelengths that is transmitted through the optical limiting structure of the sensor device.

Figure 9:
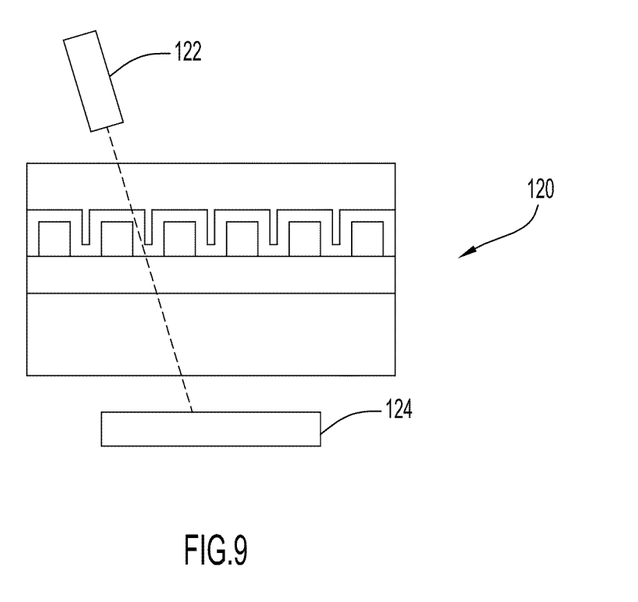
FIG. 9 schematically depicts an optical sensor in accordance with the invention including a light source and light detector.

During operation of the sensor device 120, when a target compound of interest, such as phosphorus-containing organic compound (e.g., VX or Sarin), comes in contact with the optical sensor 120, molecules of the target compound are captured within the pockets of the dendritic-metal structure layer 112 and are decomposed (e.g., by hydrolysis at the phosphorus bond for a phosphorus-containing organic compound). This decomposition reaction releases heat, which results in a temperature change above the critical temperature of the underlying VO$_2$ layer 110, resulting in a phase transition of the VO$_2$ layer and a corresponding shift in the wavelength optical extinction range for the optical limiting structure. The light projected by the light source 122 can be projected at a wavelength that is within the shifted optical extinction range of the combined phase-change material and metal particle layers, such that the phase shift of the VO$_2$ layer caused by the decomposition reaction of the target compound results in a blocking or substantial limiting of light originating from the light source 122 from being transmitted through the sensor device 120. The failure of the detector 124 to detect light at a sufficient intensity from the light source 122 provides an indication of the detection and presence of the target phosphorus compound.

Any suitable indicator mechanism can be provided with the sensor device for providing an indication to a user in the field that a particular target species has been detected. For example, any suitable type(s) of audio and/or visual indicators (e.g., beeping sound, display screen, flashing light, etc.) can be integrated with the sensor device to be actuated when the detector of the sensor device detects the presence of a target compound in the vicinity of the sensor device (i.e., by detection of the phase shift of the optical limiting layer caused by the decomposition reaction of the target compound of interest).

The optical sensor of the present invention can be designed to facilitate rapid detection and identification of one or a number of different target compounds (e.g., one or more different phosphorus-containing organic species, such as chemical and biological nerve agents like Sarin and VX as well as other dangerous phosphorus-containing organic compounds). The optical sensor device can be automated and further designed to be portable for easy transport and use in the field by an operator, with minimal sample collection required for detection and identification by the sensor device.

The dendron structure of the dendritic-metal layer does not engage in the hydrolysis reaction but instead provides sites within the pockets of the dendron structure for capturing and decomposing target molecules. The catalyst structure (e.g., the metal ions within pockets of the dendron structure or the metal or metal oxide structure to which the dendron structure is attached) further does not react with the target molecule but instead catalyzes its decomposition. The dendritic-metal layer is therefore not modified and does not require regeneration during the use of the sensor device. The dendritic-metal layer is also "self-cleaning" in that the target molecule is released from the dendron pockets after decomposition. The combination of the dendritic-metal layer being "self-cleaning" with the reversibility of the phase-change material in transitioning between optical states facilitates a restoration of the sensor device to substantially its former or original state prior to capture of the target molecule. The dendron structure can further be designed to have high selectivity to certain target compounds of interest, by modification of the dendron structure and/or the catalyzing metal or metal oxide materials used to form the dendritic-metal layer.

In addition, the dendritic-metal layer can be designed with arrays of different dendrons which target different organic compounds of interest disposed over the optical limiting structure, so that the sensor device is capable of specifically targeting a number of different organic compounds with selectivity for each different compound based upon the different dendrons provided for the sensor device. In example embodiments, the dendritic-metal layer can be designed with arrays of different dendrons that detect/decompose multiple chemical compounds in a manner so as to mimic metabolomic or proteomic processes, such that a combined response from the structural array can be used to identify a particular biological species.

The underlying optical limiting structure can also be designed to include sections with different phase-change materials and/or phase-change materials with different dopants such that the optical transition states of the optical limiting structure differ (with respect to critical temperature and/or wavelength ranges at which optical extinction occurs) at varying locations along the optical limiting structure, where these different sections of the optical limiting structure correspond with locations of the dendritic-metal layer that include different dendrons that target different organic compounds. Thus, the sensor device can be designed to have selectivity with respect to two or more different organic compounds and also a corresponding detection system that detects the presence and also identifies a specific target compound to the operator of the sensor device.

The sensor device of the present invention can be formed as a thin, nanosized structure that is useful in a variety of applications. For example, the sensor device can be integrated into a variety of different sensor systems that incorporate nanostructured and/or other multi-functional surfaces including, without limitation, surface-enhanced Raman spectroscopy (SERS) devices, microporous waveguides with SPR functionality, sensors for radiological or nuclear materials.

Having described example embodiments of an optical sensor device and methods of forming the optical sensor device, variations and changes will be suggested to those skilled in the art in view of the teachings set forth herein. It is therefore to be understood that all such variations, modifications and changes are believed to fall within the scope of the present invention as defined by the appended claims.

What is claimed:

1. A sensor device comprising:
   an optical limiting structure comprising a metal layer including at least one metal particle having a size no greater than about 1500 nanometers, and a phase-change material layer disposed adjacent at least a portion of the metal layer, the phase-change material layer comprising a phase-change material; and
   a dendritic-metal layer disposed over at least a portion of the phase-change material layer of the optical limiting structure, the dendritic-metal layer comprising an organic compound including branching chain amino acid groups attached to a metal structure;
   wherein the optical limiting structure is configured to transition from a first optical state to a second optical state when the phase-change material is heated above a critical temperature, with transmittance of light at a predetermined wavelength through the optical limiting structure being lower at the second optical state of the optical limiting structure in relation to the first optical state of the optical limiting structure.

2. The sensor device of claim 1, wherein the phase-change material comprises vanadium oxide.

3. The sensor device of claim 1, wherein the phase-change material comprises a thermochromic material that is doped with at least one of tungsten, fluorine, titanium and chromium.

4. The sensor device of claim 1, wherein metal particles of the metal layer comprise at least one of gold, platinum, palladium, silver, copper and aluminum.

5. The sensor device of claim 1, wherein the phase-change material layer has a thickness ranging from about 10 nanometers to about 50 nanometers.

6. The sensor device of claim 1, wherein the metal layer of the optical limiting structure comprises an array of metal particles having cross-sectional dimensions ranging from about 20 nanometers to about 250 nanometers.

7. The sensor device of claim 1, wherein the organic compound including branching chain amino acid groups is attached to a metal structure via a sulfide group.

8. The sensor device of claim 1, wherein the branching chain amino acid groups of the dendritic-metal layer comprise at least one of lysine and histidine.

9. The sensor device of claim 1, wherein spaces are defined between branching chain amino acid groups of the organic compound which facilitate capture and catalytic decomposition of a target phosphorus-containing compound, and the phase-change material is configured such that heat generated by the catalytic decomposition of the target phosphorus-containing compound heats the phase-change material above the critical temperature.

10. The sensor device of claim 9, wherein the spaces defined between branching chain amino acid groups of the organic compound are complexed with metal ions.

11. The sensor device of claim 10, wherein the metal ions comprise at least one of zinc ions and cobalt ions.

12. The sensor device of claim 1, wherein the metal structure of the dendritic-metal layer comprises at least one of gold, platinum, palladium, silver, copper, aluminum, zinc and titanium.

13. The sensor device of claim 1, further comprising:
   a light source oriented with respect to a first side of the optical limiting structure that projects a light at the predetermined wavelength toward the optical limiting structure; and
   a detector oriented with respect to a second side of the optical limiting structure that opposes the first side.

14. A method of providing an optical sensor device, the method comprising:
   providing a metal layer comprising a plurality of metal particles spaced from each other and forming an array, the metal particles having sizes no greater than about 1500 nanometers; and
   depositing a phase-change material layer over at least a portion of the metal layer, the phase-change material layer comprising a phase-change material that transitions from a first optical state to a second optical state, wherein transmittance of light at one or more wavelengths through the phase-change material is lower at the second optical state in relation to the first optical state;
   applying a dendritic-metal layer over at least a portion of the phase-change material layer of the optical limiting structure, the dendritic-metal layer comprising an organic compound including branching chain amino acid groups attached to a metal structure;

wherein the optical limiting structure is configured to transition from a first optical state to a second optical state when the phase-change material is heated above a critical temperature, with transmittance of light at a predetermined wavelength through the optical limiting structure being lower at the second optical state of the optical limiting structure in relation to the first optical state of the optical limiting structure.

15. A method of detecting the presence of a phosphorus-containing organic compound with an optical sensor device, the sensor device comprising an optical limiting structure including a metal layer with at least one metal particle having a size no greater than about 1500 nanometers, and a phase-change material layer that includes a phase-change material and that is disposed adjacent at least a portion of the metal layer, and a dendritic-metal layer disposed over at least a portion of the phase-change material layer of the optical limiting structure, the dendritic-metal layer including an organic compound including branching chain amino acid groups attached to a metal structure, the method comprising:
 capturing and decomposing a phosphorus-containing organic compound via the dendritic-metal layer, wherein the decomposition of the phosphorus-containing organic compound captured by the dendritic-metal layer initiates a transition of the optical limiting structure from a first optical state to a second optical state; and
 detecting a transition of the optical limiting structure from the first optical state to the second optical state.

16. The method of claim 15, wherein the dendritic-metal layer is configured to capture and decompose organophosphate compounds.

17. The method of claim 16, wherein the organophosphate compounds comprise at least one of VX and sarin.

18. The method of claim 17, wherein the dendritic-metal layer is configured to capture and decompose phosphorus-containing organic compounds by decomposition via at least one of a phosphorus-oxygen bond, a phosphorus-sulfur bond, a phosphorus-cyano bond and a phosphorus-fluorine bond.

19. The method of claim 15, wherein the branching chain amino acid groups of the dendritic-metal layer comprise at least one of lysine and histidine.

20. The method of claim 15, wherein transmittance of light at a predetermined wavelength through the optical limiting structure is lower at the second optical state of the optical limiting structure in relation to the first optical state of the optical limiting structure, and the detection of a transition of the optical limiting structure from the first optical state to the second optical state comprises:
 projecting light at the predetermined wavelength toward the optical limiting structure; and
 determining an amount of light at the predetermined wavelength that is transmitted through the optical limiting structure.

* * * * *